United States Patent [19]

Sung et al.

[11] 4,305,731
[45] Dec. 15, 1981

[54] AMINOALKYLIMIDAZOLINE DERIVATIVES OF A SARCOSINE COMPOUND AND A FUEL COMPOSITION CONTAINING SAME

[75] Inventors: Rodney L. Sung, Fishkill; Peter Dorn, Lagrangeville, both of N.Y.

[73] Assignee: Texaco Inc., White Plains, N.Y.

[21] Appl. No.: 196,891

[22] Filed: Oct. 14, 1980

[51] Int. Cl.³ .............................................. C10L 1/22
[52] U.S. Cl. ...................................... 44/63; 252/392; 548/353
[58] Field of Search .......................... 548/353; 44/63; 252/392

[56] References Cited

U.S. PATENT DOCUMENTS

| | | | |
|---|---|---|---|
| 2,919,979 | 1/1960 | Martin et al. | 44/63 |
| 3,033,664 | 5/1962 | Pethrick et al. | 44/63 |
| 3,337,472 | 8/1967 | Littler et al. | 44/63 |
| 3,409,646 | 11/1968 | Sims et al. | 548/353 |
| 3,705,027 | 12/1972 | Adams et al. | 44/63 |
| 4,137,416 | 1/1979 | Panzer et al. | 548/353 |

Primary Examiner—Winston A. Douglas
Assistant Examiner—Y. Harris-Smith
Attorney, Agent, or Firm—Carl G. Ries; Robert A. Kulason; James J. O'Loughlin

[57] ABSTRACT

An additive represented by the following formula:

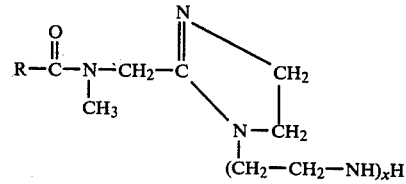

in which R is a hydrocarbon radical having from about 10 to 20 carbon atoms and x is a value from 1 to 3, and a corrosion inhibited and detergent fuel composition containing such additive.

11 Claims, No Drawings

AMINOALKYLIMIDAZOLINE DERIVATIVES OF A SARCOSINE COMPOUND AND A FUEL COMPOSITION CONTAINING SAME

BACKGROUND OF THE INVENTION

1. Field of the Invention

Gasoline compositions are highly refined products. Despite this, they contain minor amounts of impurities which can promote corrosion during the period that the fuel is transported in bulk or held in storage. Corrosion can also occur in the fuel tank, fuel lines and carburetor of a motor vehicle. As a result, a commercial motor fuel composition must contain a corrosion inhibitor to inhibit or prevent corrosion.

Internal combustion engine design is undergoing changes to meet new standards for engine exhaust gas emissions. One design change involves the feeding of blow-by gases from the crankcase zone of the engine into the intake air supply to the carburetor rather than venting these gases to the atmosphere as in the past. Another change involves free cycling part of the exhaust gases to the combustion zone of the engine in order to minimize objectionable emissions. Both the blow-by gases from the crankcase zone and the recycled exhaust gases contains significant amounts of deposit forming substances which promote the formation of deposits in and around the throttle plate area of the carburetor. These deposits restrict the flow of air through the carburetor and at low speeds so that an overrich fuel mixture results. This condition produces rough engine idling or stalling causing an increase in the amount of polluting exhaust gas emissions, which the engine design changes were intended to overcome, and decreasing fuel efficiency.

An acceptable motor fuel contains additives addressed to correcting or inhibiting these disabling characteristics of motor fuel. Thus, the discovery of novel and compatible motor fuel additives capable of general application and selective modification to accommodate changing demands while combining good detergency properties with effective corrosion inhibition will provide a material advance in the state of the art.

The prior art discloses derivatives of N-acylsarcosine as corrosion inhibitors for fuel compositions. It has been found, however, that these compounds can be completely extracted into the caustic water bottoms encountered in gasoline manufacture. Consequently, the fuels lose their corrosion inhibiting property just when this property is most needed. A novel N-acylsarcosine derivative has been found which mitigates or overcomes the problem of extraction by caustic water bottoms during manufacture and which provides a motor fuel composition having valuable corrosion inhibition and carburetor detergent properties.

2. Discussion of the Prior Art

U.S. Pat. No. 2,919,979 discloses a rust inhibited motor fuel composition containing a simple mixture of an acylsarcosine and a 1,2-disubstituted imidazoline. U.S. Pat. No. 3,033,664 discloses an anti-icing motor fuel composition containing a 1,2, di-substituted imidazoline.

SUMMARY OF THE INVENTION

The novel detergent and anti-corrosion additive composition of the invention is a 1-aminoethyl imidazoline derivative of a sarcosine represented by the following formula:

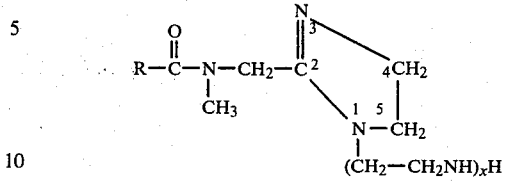

in which R is a monovalent hydrocarbon radical having from about 10 to 20 carbon atoms and X has a value from 1 to 3.

The motor fuel composition of the invention which has improved detergency and anti-corrosion characteristics comprises a mixture of hydrocarbons boiling in the gasoline boiling range and a minor amount of the prescribed imidazoline derivative of a sarcosine.

PREFERRED EMBODIMENTS OF THE INVENTION

The aminoalkylimidazoline sarcosine derivative compound of the invention is prepared by reacting an N-acyl sarcosine compound with a polyalkylene polyamine. The N-acyl sarcosine precursor which can be employed to prepare the prescribed aminoalkylimidazoline derivative of the invention is represented by the following formula:

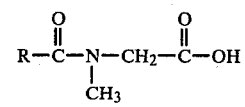

in which R is a saturated or unsaturated monovalent hydrocarbon radical which is called N-acylsarcosine or N-acyl-N-methyl glycine having from about 10 to 20 carbon atoms. The preferred N-acyl sarcosine precursor is one in which the hydrocarbon radical is a saturated aliphatic hydrocarbon radical having from about 12 to 18 carbon atoms. Specific N-acylsarcosine precursor compounds for preparing the novel additive compound of the invention include:

|   | | |
|---|---|---|
|   | N-lauroyl sarcosine | (Sarkosyl L); |
|   | N-cocoyl sarcosine | (Sarkosyl CC); |
|   | N-oleoyl sarcosine | (Sarkosyl O); |
| and | N-stearoyl sarcosine | (Sarkosyl S) |

The polyalkylene polyamine reactant for making the novel compound of the invention is represented by the formula:

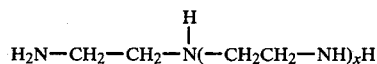

in which x has a value from 1 to 3. Specific compounds of this group include diethylenetriamine, triethylenetetra amine and tetraethylenepentamine.

The prescribed N-acyl sarcosine precursor and the polyalkylene polyamine are reacted by mixing them together in an inert hydrocarbon solvent, such as xylene, and refluxing the reaction mixture at an elevated temperature ranging between 130° to 140° C. for a sufficient length of time to effect the reaction. During the reaction period, which can be for 8 hours or more, the water of reaction is removed overhead as an azeotropic mixture. Thereafter, the solvent and any unreacted reagents are stripped from the reaction product under a vacuum leaving the desired product.

The amino alkyl imidazoline derivative of a sarcosine compound of the invention is represented by the formula:

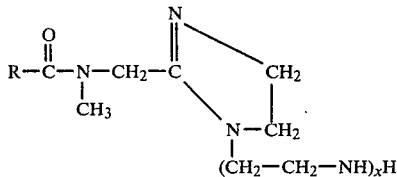

in which R is a monovalent hydrocarbon radical having from 10 to 20 carbon atoms and x has a value from 1 to 3.

The following examples illustrate the method for preparing the novel additive of this invention.

EXAMPLE I

1-Aminoethyl imidazoline derivative of N-oleoyl sarcosine: a mixture of 0.8 moles of N-oleyl sarcosine, 0.8 moles of diethylene triamine (DETA) and 11 moles of xylene was refluxed and the water of the reaction separated by an azeotrope distillation over a reaction period of eight hours. The reaction product was then stripped of solvent under vacuum and recovered. The product, 1-aminoethyl imidazoline of N-oleoyl sarcosine, was identified by infrared and elemental analysis. The results of these analyses are as follows:

| % N | 13 |
| --- | --- |
| Mol. Wt. | 483 |

EXAMPLE II

1-Aminoethyl imidazoline derivative to N-lauroyl sarcosine: a mixture of 0.8 moles of lauryl sarcosine, 0.8 moles of diethylene triamine (DETA), and 11 moles of xylene is refluxed and the water of the reaction is separated by an azeotrope distillation over the 8 hour reaction period. At the end of that period the reaction product is stripped of solvent under vacuum and recovered. The product, 1-aminoethyl imidazoline of N-lauroyl sarcosine, is then analyzed by infrared and elemental analysis. The results of these analyses are as follows:

| % N | .17 |
| --- | --- |
| Mol. Wt. | 318 |

Other effective aminoalkyl imidazoline derivatives of an N-acyl sarcosine within the scope of this invention include 1-amino ethyl imidazoline of lauroyl sarcosine; 1-amino ethyl imidazoline of oleoyl sarcosine; 1-amino ethyl imidazoline of stearoyl sarcosine; 1-(diethylene diamine) imidazoline of lauroyl sarcosine; 1-(diethylene diamine) imidazoline of aleoyl sarcosine; 1-(triethylene triamine) imidazoline of lauroyl sarcosine; 1-(triethylene triamine) imidazoline of oleoyl sarcosine; and 1-(triethylene triamine) imidazoline of stearoyl sarcosine.

The base fuel in which the additive of the invention is employed is a mixture of hydrocarbons boiling in the gasoline boiling range. This base fuel may consist of straight chain or branched chain paraffins, cycloparaffins, olefins, and aromatic hydrocarbons or any mixture of these. The base fuel can be derived from straight-run naphtha, polymer gasoline, natural gasoline or from catalytic fully reformed stock and boiled in the range from about 80° to 450° F. The composition and the octane level of the base fuel are not critical any any conventional motor fuel base can be employed in the process of this invention.

The fuel composition of the invention may contain any of the additives normally employed in a motor fuel. For example, the base fuel may be blended with an anti-knock compound, such as tetraalkyl lead compound, including tetraethyllead, tetramethyllead, tetrabutyllead and mixtures thereof. The fuel composition can also contain anti-icing additives, dyes, upper cylinder lubricating oils and the like.

The additive composition is employed in the motor fuel composition of the invention in a concentration ranging from about 0.0002 to about 0.2 weight percent based on the weight of the motor fuel composition. It is preferred to employ the additive in a concentration ranging from 0.008 to 0.01 weight percent with the most preferred concentration being 0.008 weight percent. These weight percent concentrations are equivalent respectively to about 0.5 to 500 PTB (pounds of additive per 1000 barrels of gasoline) or 2 to 30 PTB with the most preferred being around 20 PTB.

Gasoline blends were prepared from a typical base fuel mixed with specified amounts of the prescribed fuel additive of the invention. These fuels were then tested to determine the effectiveness of the additive in gasoline. The results obtained in this test using a commercial detergent gasoline are also given.

The base fuel employed for demonstrating the detergency effectiveness of the additive composition of the invention was an unleaded grade gasoline having a research octane number of about 93. This gasoline consisted of about 30% aromatic hydrocarbon, 8% olefinic hydrocarbon and 62% paraffinic hydrocarbon and boiled in the range from 100° F. to 380° F.

The effect on carburetor detergency of the fuel composition of the invention was determined in the Buick Carburetor Detergency Test. This test is run on a Buick 350 CID V-8 engine equipped with a two barrel carburetor. The engine is mounted on a test stand and has operating EGR and PVC systems. The test cycle, shown in Table II, is representative of normal road operation. Approximately 300 gallons of fuel and three quarters of oil are required for each run.

Prior to each run the carburetor is completely reconditioned. Upon completion of the run the throttle plate deposits are visually rated according to a CRC Varnish rating scale where 1 describes heavy deposits on the throttle plate and 10 a completely clean plate. The area below the plates is similarly rated.

TABLE I

| 1973 BUICK CARBURETOR DETERGENCY TEST OPERATING CONDITIONS | | | |
| --- | --- | --- | --- |
|  | Stage I | Stage II | Stage III |
| Duration, hours | 1 | 1 | 1 |
| Speed, r.p.m. | 650 ± 25 | 1500 ± 25 | 2000 ± 25 |
| Torque, ft.-lbs. | 0 | 80 ± 2 | 108 ± 2 |
| Water Out, °F. | 205 ± 5 | 205 ± 5 | 205 ± 5 |
| Carburetor Air, °F. | 140 ± 5 | 140 ± 5 | 140 ± 5 |
| Exhaust Back Pres. in Hg. | — | 0.7 ± 0.1 | — |
| Man. Vac. in Hg. | — | 15.8 | 14.2 |
| Fuel Flow, lbs/hr | 0.7 | 7.5 | 12.0 |

TABLE I-continued
1973 BUICK CARBURETOR DETERGENCY TEST OPERATING CONDITIONS

|  | Stage I | Stage II | Stage III |
|---|---|---|---|
| Test Duration, 120 hours | | | |

The results of this test are set forth in the following table:

TABLE II
BUICK CARBURETOR DETERGENCY TEST

| Run | Fuel Composition | Additive Concentration | Carburetor Rating Average Plates/Below Plates |
|---|---|---|---|
| 1 | Base Fuel | None | 3.6 |
| 2 | " | 20 PTB[2] of the product of Example I | 7.2 |
| 3 | " | 30 PTB of a competitive rust inhibiting and detergent additive | 7.2 |
| 4 | " | 76 PTB commercial rust inhibiting and detergent additive | 6.1 |
|   |   | None | 3.6 |

[1] 10 = clean, 1 = dirty
[2] PTB = Pounds of additive per 1000 barrels of fuel.

The foregoing results demonstrate that the novel fuel composition of the invention was surprisingly effective for achieving carburetor cleanliness as measured by the CRC Varnish rating scale in the Buick Carburetor Detergency Test.

The rust inhibiting effect of the fuel composition of the present invention was determined in the National Association of Corrosion Engineers Test (NACE).

In this test a mixture of 300 ml of test gasoline and 30 ml distilled water is stirred at a temperature of 37.8° C. (100° F.) with a steel specimen completely immersed therein for a test period of 3½ hours. The percentage of the specimen that has rust is determined visually and noted.

The results of this test are set forth in the following table:

TABLE III
NACE RUST TEST

| Additive in Unleaded Base Fuel | % Rust[a] |
|---|---|
| None | 50-100 ck 50-100 |
| 5 PTB[c] of the product of Example I | Tr-1[b], Tr-1 |
| 10 PTB of the product of Example I | Tr, Tr |
| 76 PTB commercial rust inhibitor | Tr, Tr |

[a] less than 5% passes test
[b] Tr = Trace
[c] PTB = Pounds of additive per 1000 barrels of fuel.

The foregoing results demonstrate that the novel fuel composition of the invention was surprisingly effective where preventing the formation of rust in the corrosion of the metal surfaces with which the fuel was in contact.

We claim:

1. A compound comprising an amino alkyl imidazoline derivative of a sarcosine compound represented by the following formula:

$$R-\overset{O}{\overset{\|}{C}}-\underset{CH_3}{\overset{|}{N}}-CH_2-\overset{N}{\overset{\|}{C}}\diagdown\begin{array}{c}CH_2\\ \\ N-CH_2\\ |\\ (CH_2-CH_2-NH)_xH\end{array}$$

where R is a hydrocarbyl radical having 10 to 20 carbon atoms and x has a value from 1 to 3.

2. A compound according to claim 1 in which R is a hydrocarbyl radical having 12 to 18 carbon atoms.

3. A compound according to claim 1 in which R is a hydrocarbyl radical having 15 to 18 carbon atoms.

4. A compound according to claim 1 in which R is a hydrocarbyl radical having 17 carbon atoms.

5. A motor fuel composition comprising a mixture of hydrocarbons boiling in the gasoline boiling range containing an amino alkyl imidazoline derivative of a sarcosine compound represented by the formula:

$$R-\overset{O}{\overset{\|}{C}}-\underset{CH_3}{\overset{|}{N}}-CH_2-\overset{N}{\overset{\|}{C}}\diagdown\begin{array}{c}CH_2\\ \\ N-CH_2\\ |\\ (CH_2-CH_2-NH)_xH\end{array}$$

where R is a hydrocarbyl radical having 10 to 20 carbon atoms and x has a value from 1 to 3.

6. A motor fuel composition according to claim 5 in which R is a hydrocarbyl radical having from 12 to 18 carbon atoms.

7. A motor fuel composition according to claim 5 in which R is a hydrocarbyl radical having 15 to 18 carbon atoms.

8. A motor fuel composition according to claim 5 in which R is a hydrocarbyl radical having 17 carbon atoms.

9. A motor fuel composition according to claim 5 containing from about 0.0002 to 0.2 weight percent of the additive.

10. A motor fuel composition according to claim 5 containing from about 0.0008 to 0.01 weight percent of the additive.

11. A motor fuel composition according to claim 5 containing from about 0.002 to 0.008 weight percent of the additive.

* * * * *